United States Patent [19]
Ratz

[11] Patent Number: 6,008,412
[45] Date of Patent: Dec. 28, 1999

[54] PROCESS TO MAKE CHIRAL COMPOUNDS

[75] Inventor: Andrew Michael Ratz, Greenwood, Ind.

[73] Assignee: Eli Lilly and Company, Indianapolis, Ind.

[21] Appl. No.: 09/277,117

[22] Filed: Mar. 26, 1999

Related U.S. Application Data

[63] Continuation-in-part of application No. 09/151,114, Sep. 10, 1998, abandoned
[60] Provisional application No. 60/061,798, Oct. 14, 1997.

[51] Int. Cl.$^6$ .................................................. C07G 209/88
[52] U.S. Cl. .......................... 564/425; 564/285; 564/287; 564/363
[58] Field of Search .................................... 564/285, 287, 564/363, 425

[56] References Cited

U.S. PATENT DOCUMENTS 4,765,826  8/1988  Van Heertum et al. .................. 71/121
5,527,821  6/1996  Willman et al. ........................ 514/428

FOREIGN PATENT DOCUMENTS 0 391 070  10/1990  European Pat. Off. .
0 457 559  11/1991  European Pat. Off. .
95 02574   1/1995   WIPO .

OTHER PUBLICATIONS

Robertson, D. W., et al., Absolute Configurations and Pharmaceutical Activities of the Optical Isomers of Fluoxetine, A Selective Serotonin–Uptake Inhibitor Journal of Medicinal Chemistry, vol. 31, No. 7, Jul. 1, 1988, pp. 1412–1417.

*Primary Examiner*—Peter O'Sullivan
*Attorney, Agent, or Firm*—David M. Stemerick

[57] ABSTRACT

The present invention relates to processes for resolving N-methyl-3(R,S)-hydroxy-3-phenylpropylamine and N,N-dimethyl-3 (R,S)-hydroxy-3-phenylpropylamine with the isomers of mandelic acid and the resulting salts.

8 Claims, No Drawings

PROCESS TO MAKE CHIRAL COMPOUNDS

PRIORITY INFORMATION

This application is a continuation-in-part of U.S. patent application Ser. No. 09/151,114, filed Sep. 10, 1998, now abandoned which claims the benefit of priority of U.S. Provisional patent application No. 60/061,798, filed Oct. 14, 1997.

FIELD OF THE INVENTION

This invention relates to the art of synthetic organic chemistry. Specifically, the invention is a process to separate enantiomers from a mixture so that the individual enantiomers can be used in the syntheses of valuable chiral pharmaceutical compounds.

BACKGROUND OF THE INVENTION

The structural formula:

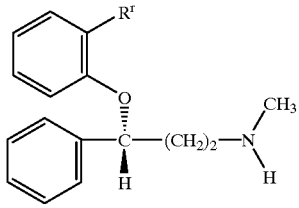

represents N-methyl-3 R-(2-methylphenoxy)-3-phenylpropylamine when $R^r$ is methyl, and represents N-methyl-3 R-(2-methylthiophenoxy)-3-phenylpropylamine, when $R^r$ is methylthio. Both N-methyl-3 R-(2-methylphenoxy)-3-phenylpropylamine and N-methyl-3 R-(2-methylthiophenoxy)-3-phenylpropylamine act as selective and potent inhibitors of norepinephrine uptake.

Syntheses of N-methyl-3 R-(2-methylphenoxy)-3-phenylpropylamine are described in U.S. Pat. Nos. 4,018,895, 4,194,009, 4,314,081 and 4,777,291, the disclosures of which are hereby incorporated by reference. A synthesis of N-methyl-3 R-(2-methylthiophenoxy)-3-phenylpropylamine is described in U.S. Pat. No. 5,281,624, the disclosure of which is hereby incorporated by reference.

The structural formula:

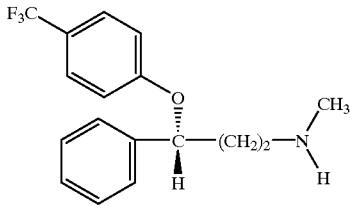

represents N-methyl-3 R-(4-trifluoromethylphenoxy)-3-phenylpropylamine, (R)-fluoxetine.

Syntheses of (R)-fluoxetine, (R)-N-methyl-3-(4-trifluoromethylphenoxy)-3-phenylpropylamine, are known in the art and taught in U.S. Pat. No. 5,708,035.

In known syntheses of these compounds either a mixture comprising both the R and S enantiomers of the desired compound is formed and then the desired enantiomer is separated from the mixture using techniques known in the art or the desired enatiomer is prepared directly from a chiral substrate. It is desirable to develop an alternate process that allows for making of the individual enantiomers directly.

SUMMARY OF THE INVENTION

This invention refers to a process to make the S-(+)-mandelic acid salt of N-methyl-3 R-hydroxy-3-phenylpropylamine comprising reacting N-methyl-3(R,S)-hydroxy-3-phenylpropylamine with S-(+)-mandelic acid.

This invention also refers to a process to make the R-(−)-mandelic acid salt of N-methyl-3 S-hydroxy-3-phenylpropylamine comprising reacting N-methyl-3 (R,S)-hydroxy-3-phenylpropylamine with R-(−)-mandelic acid.

This invention refers to a process to make the R-(−)-mandelic acid salt of N,N-dimethyl-3 R-hydroxy-3-phenylpropylamine comprising reacting N,N-dimethyl-3 (R,S)-hydroxy-3-phenylpropylamine with R-(−)-mandelic acid.

This invention also refers to a process to make the S-(+)-mandelic acid salt of N,N-dimethyl-3 S-hydroxy-3-phenylpropylamine comprising reacting N,N-dimethyl-3 (R,S)-hydroxy-3-phenylpropylamine with S-(+)-mandelic acid.

This invention also refers to a compound of the formula:

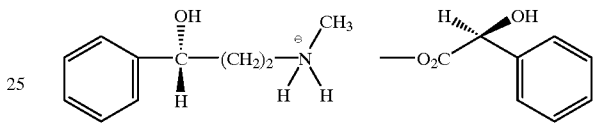

which is named N-methyl-3 R-hydroxy-3-phenylpropylamine S-(+)-mandelate salt.

This invention also refers to a compound of the formula:

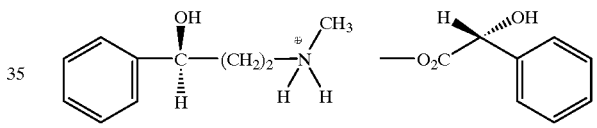

which is named N-methyl-3 S-hydroxy-3-phenylpropylamine R-(−)-mandelate salt.

This invention also refers to a compound of the formula:

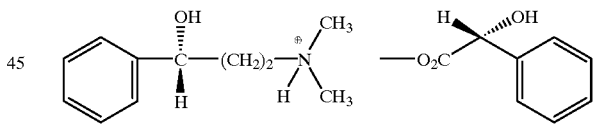

which is named N,N-dimethyl-3 R-hydroxy-3-phenylpropylamine R-(−)- mandelate salt.

This invention also refers to a compound of the formula:

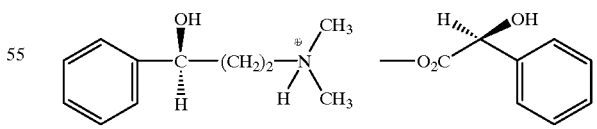

which is named N,N-dimethyl-3 S-hydroxy-3-phenylpropylamine S-(+)-mandelate salt.

This invention also refers to a process to make N-methyl-3 R-(2-methylphenoxy)-3-phenylpropylamine; the improvement comprising using N-methyl-3 R-hydroxy-3-phenylpropylamine S-(+)-mandelate salt in the synthesis.

This invention also refers to a process to make N-methyl-3 R-(4-trifluoromethylphenoxy)-3- phenylpropylamine; the improvement comprising using N-methyl-3 R-hydroxy-3-phenylpropylamine S-(+)-mandelate salt in the synthesis.

This invention also refers to a process to make N-methyl-3 S-(4-trifluoromethylphenoxy)-3-phenylpropylamine; the improvement comprising using N-methyl-3 S-hydroxy-3-phenylpropylamine R-(−)-mandelate salt in the synthesis.

This invention also refers to a process to make N-methyl-3 R-(2-methylthiophenoxy)-3-phenylpropylamine; the improvement comprising using N-methyl-3 R-hydroxy-3-phenylpropylamine S-(+)-mandelate salt in the synthesis.

This invention also refers to a process to make N-methyl-3 R-(4-trifluoromethylphenoxy)-3-phenylpropylamine; the improvement comprising using N,N-dimethyl-3 R-hydroxy-3-phenylpropylamine R-(−)-mandelate salt in the synthesis.

This invention also refers to a process to make N-methyl-3 S-(4-trifluoromethylphenoxy)-3-phenylpropylamine; the improvement comprising using N,N-dimethyl-3 S-hydroxy-3-phenylpropylamine S-(+)-mandelate salt in the synthesis.

This invention also refers to a process to make N-methyl-3 R-(2-methylthiophenoxy)-3-phenylpropylamine; the improvement comprising using N,N-dimethyl-3 R-hydroxy-3-phenylpropylamine R-(−)-mandelate salt in the synthesis.

DETAILED DESCRIPTION OF THE INVENTION

N-methyl-3(R,S)-hydroxy-3-phenylpropylamine refers to a compound of the formula:

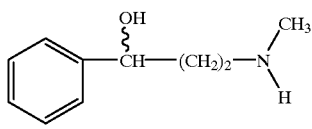

N,N-dimethyl-3(R,S)-hydroxy-3-phenylpropylamine refers to a compound of the formula:

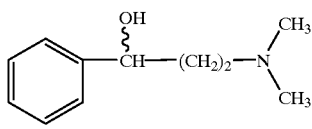

S-(+)-mandelic acid refers to a compound of the formula:

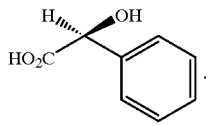

R-(−)-mandelic acid refers to a compound of the formula:

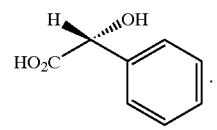

N-methyl-3 R-hydroxy-3-phenylpropylamine S-(+)-mandelate salt refers to a compound of the formula:

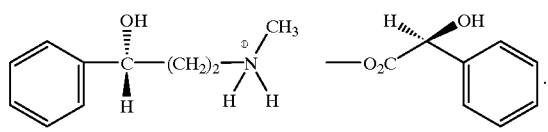

N-methyl-3 S-hydroxy-3-phenylpropylamine R-(−)-mandelate salt refers to a compound of the formula:

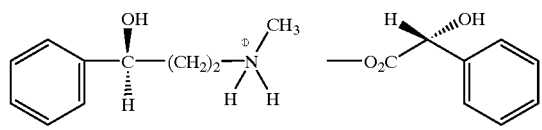

N,N-dimethyl-3 R-hydroxy-3-phenylpropylamine S-(+)-mandelate salt refers to a compound of the formula:

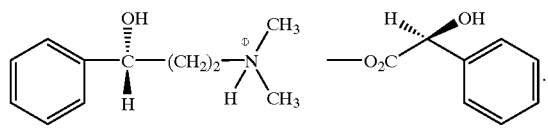

N,N-dimethyl-3 S-hydroxy-3-phenylpropylamine R-(−)-mandelate salt refers to a compound of the formula:

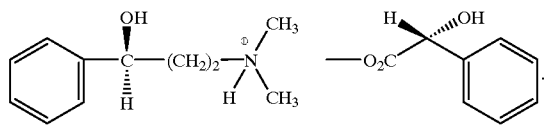

Unless otherwise noted, all reactions described herein are preferably conducted under an inert atmosphere. The preferred inert atmosphere is nitrogen.

The process to make the S-(+)-mandelate salt of N-methyl-3 R-hydroxy-3-phenylpropylamine begins with the compound N-methyl-3(R,S)-hydroxy-3-phenylpropylamine (hereinafter PMAP). A synthesis of PMAP is described in European Pat. Application No. 90104018.8.

PMAP is reacted with S-(+)-mandelic acid in order to make N-methyl-3 R-hydroxy-3-phenylpropylamine S-(+)-mandelate salt. S-(+)-mandelic acid is available commercially. The salt-forming reaction is conducted in a solvent. The solvent is selected from the group consisting of inert organic solvents, including, but not limited to, toluene, benzene, xylene, ethyl acetate, acetone (dimethylketone, DMK), methyl-tert-butyl ether, ethanol and mixtures thereof. The preferred solvent is ethyl acetate. The process is conducted at a temperature of from about 25° C. to about 78° C. The preferred temperature is from about 50° C. to about 55° C. The reaction is conducted for a time period of from about five minutes to about 1 hour. When the reaction temperature is from about 50° C. to about 55° C. the preferred time for the reaction is about five minutes. After five minutes at from about 50° C. to about 55° C. the reaction mixture is actively cooled to room temperature of about 25° C. over a period of about 24 hours. Then the mixture is held at room temperature for about one-and-a-half hours. Following this time at room temperature the solid N-methyl-3 R-hydroxy-3-phenylpropylamine S-(+)-mandelate salt may be separated from the reaction mixture using standard techniques known to one of ordinary skill in the art, such as by filtering the reaction mixture and collecting the solid.

The same procedure described above can be used to make N-methyl-3 S-hydroxy-3-phenylpropylamine R-(−)-mandelate salt; providing that R-(−)-mandelic acid is used in place of the S-(+)-mandelic acid that is used to make the N-methyl-3 R-hydroxy-3-phenylpropylamine S-(+)-mandelate salt.

While virtually any molar ratio of PMAP to the respective mandelic acid provides an operational process, it is preferred that from about 0.2 to 2 molar equivalents of the mandelic acid be used per mole of PMAP. While, for example, approximately a 1:1 ratio of PMAP and the appropriate mandelic acid provides good results, using approximately 0.45–0.50 molar equivalents of the mandelic acid provides comparable yields with higher enantiomeric excess, i.e., such ratios result in a much purer, from an enantiomer standpoint, product.

N-methyl-3 R-hydroxy-3-phenylpropylamine S-(+)-mandelic acid can be used to make certain valuable pharmaceutical products such as N-methyl-3 R-(4-trifluoromethylphenoxy)-3-phenylpropylamine (R-fluoxetine), N-methyl-3 R-(2-methylphenoxy)-3-phenylpropylamine (tomoxetine), and N-methyl-3 R-(2-methylthiophenoxy)-3-phenylpropylamine. See, e.g., U.S. Pat. Nos. 5,104,899, 5,356,934, 5,281,624, 5,441,985 and 5,658,590 and EP Patent Application Publication 52,492. N-methyl-3 S-hydroxy-3-phenylpropylamine R-(−)-mandelic acid can be used to make certain valuable pharmaceutical products such as N-methyl-3 S-(4-trifluoromethylphenoxy)-3-phenylpropylamine (S-fluoxetine).

Accordingly, this invention also provides for a process to make N-methyl-3 R-(substituted phenoxy)-3-phenylpropylamines comprising:

(1) reacting N-methyl-3 R-hydroxy-3-phenylpropylamine S-(+)-mandelate salt with a suitable base to form an alkoxide of formula (a):

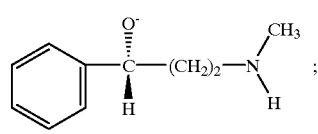

formula (a)

(2) reacting the alkoxide of formula (a) with a halobenzene compound of formula (b):

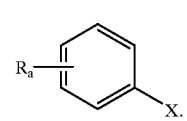

formula (b)

where X is —F or —Cl, and $R_a$ is 2-methyl, 4-trifluoromethyl, or 2-methylthio to give a compound of the formula

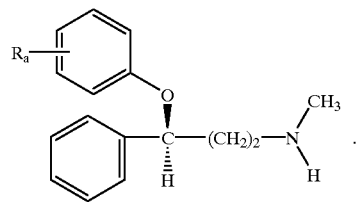

formula (c)

This process is also applicable for the similar reaction for making S-fluoxetine comprising:

(1) reacting N-methyl-3 S-hydroxy-3-phenylpropylamine R-(−)-mandelate salt with a suitable base to form an alkoxide of formula (a):

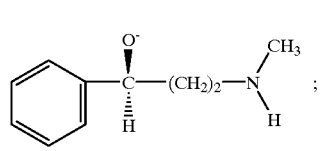

formula (a')

( 2) reacting the alkoxide of formula (a') with a 4-trifluoromethylhalobenzene compound of formula (b'):

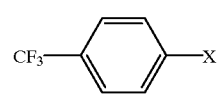

formula (b)

where X is —F or —Cl, to give a compound of the formula

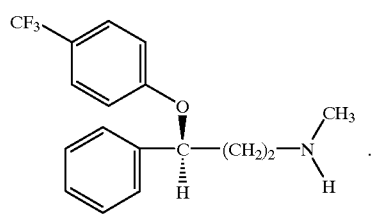

formula (c')

The process to make the R-(−)-mandelate salt of N,N-dimethyl-3 R-hydroxy-3-phenylpropylamine begins with the compound N,N dimethyl-3(R,S)-hydroxy-3-phenylpropylamine which is commercially available and is readily prepared by reduction of the Mannich product prepared by the reaction of formaldehyde, dimethylamine, and acetophenone as is known in the art.

N,N-dimethyl-3(R,S)-hydroxy-3-phenylpropylamine is reacted with R-(−)mandelic acid in order to make N,N-dimethyl-3 R-hydroxy-3-phenylpropylamine R-(−)-mandelate salt. The salt-forming reaction is conducted in a solvent. The solvent is selected from the group consisting of inert organic solvents, including, but not limited to, toluene, benzene, xylene, ethyl acetate, acetone, methyl-tert-butyl ether, ethanol and mixtures thereof. The preferred solvent is methyl-tert-butyl ether and acetone. The process is conducted at a temperature of from about 25° C. to about 80° C. The preferred temperature is from about 50° C. to about 60° C. The reaction is conducted for a time period of from about five minutes to about 1 hour. After the reaction mixture is formed it is preferably cooled slowly to give the product as a solid. N,N-dimethyl-3 R-hydroxy-3-phenylpropylamine R-(−)-mandelate salt may be separated from the reaction mixture using standard techniques known to one of ordinary skill in the art, such as by filtering the reaction mixture and collecting the solid.

The same procedure described above can be used to make N,N-dimethyl-3 S-hydroxy-3-phenylpropylamine S-(+)-mandelate salt; providing that S-(+)-mandelic acid is used in place of the R-(−)-mandelic acid that is used to make the N,N-dimethyl-3 R-hydroxy-3-phenylpropylamine R-(−)-mandelate salt.

Accordingly, this invention also provides for a process to make N-methyl-3 R-(substituted phenoxy)-3-phenylpropylamines comprising:

(1) reacting N,N-dimethyl-3 R-hydroxy-3-phenylpropylamine R-(−)-mandelate salt with a suitable base to form an alkoxide of formula (a):

formula (a1)

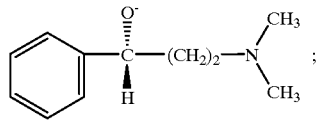

(2) reacting the alkoxide of formula (a1) with a halobenzene compound of formula (b):

formula (b)

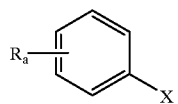

where X is —F or —Cl, and $R_a$ is 4-trifluoromethyl or 2-methylthio to give a compound of the formula formula (c1)

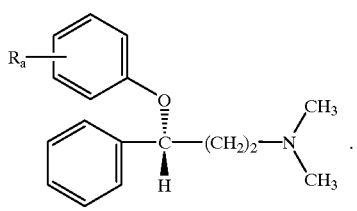

(3) N-demethylation of a compound of formula (c1) to give a compound of the formula formula (c)

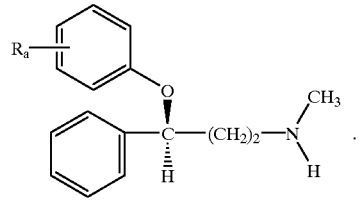

This process is also applicable for the similar reaction for making S-fluoxetine comprising:

(1) reacting N,N-dimethyl-3 S-hydroxy-3-phenylpropylamine S-(+)-mandelate salt with a suitable base to form an alkoxide of formula (a):

formula (b)

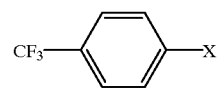

(2) reacting the alkoxide of formula (a1') with a 4-trifluoromethylhalobenzene compound of formula (b):

formula (a')

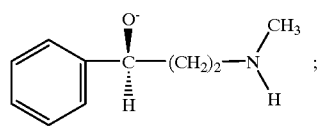

where X is —F or —Cl, to give a compound of the formula formula (c')

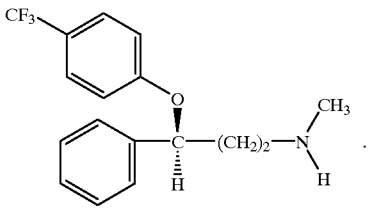

(3) N-demethylation of a compound of formula (c1g') to give a compound of the formula formula (c')

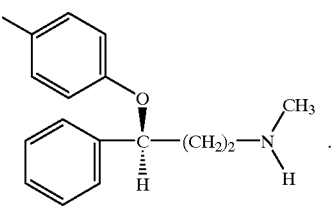

As is understood by the skilled artisan, the processes depicted in this application to prepare N-methyl-3 R-(substituted phenoxy)-3-phenylpropylamines utilizing a mandelic acid salt can be carried out on the base isolated from the mandelic acid salt, as well as, other salts prepared from the mandelic acid salt or the isolated base.

The following examples are illustrative only and are not intended to limit the scope of the invention in any way.

The terms and abbreviations used in the instant examples have their normal meanings unless otherwise designated. For example "C" refers to degrees Celsius; "%ee" refers to percent enantiomeric excess; "N" refers to normal or normality; "mmol" refers to millimole or millimoles; "g" refers to gram or grams; "d" refers to density, "min." refers to minutes; "mL" means milliliter or milliliters; "M" refers to molar or molarity; TLC refers to thin-layer chromatography, "HPLC" refers to high performance liquid chromatography; ¹H-NMR refers to proton Nuclear Magnetic Resonance, ¹³C-NMR refers to carbon-13 Nuclear Magnetic Resonance, "mm" refers to millimeters; "MTBE" refers to methyl tert-butyl ether; "cm" refers to centimeters; "nm" refers to nanometers; "PM" refers to N-methyl-3(R,S)-hydroxy-3-phenylpropylamine; "rt" refers to retention time, and vol. refers to an amount in mL/grams relative to starting material.

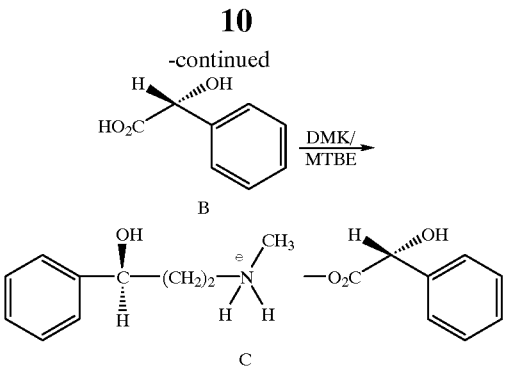

R(−)-Mandelic acid B (10.37 g, 0.0682 mol) is added in one portion to a solution of PMAP A (25.0 g, 0.152 mol) in 200 mL dimethylketone (DMK) and 200 mL of MTBE. The solution is heated to 50° C., and the solution is seeded with authentic N-methyl-3 S-hydroxy-3-phenylpropylamine R-(−)-mandelate salt. The mixture is stirred for 1 hour and then is cooled over one hour to room temperature where it is stirred for 16 hours. The mixture is filtered and crystals obtained are washed with 75 mL 1.5:1 MTBE:acetone. After drying, N-methyl-3 S-hydroxy-3-phenylpropylamine R-(−)-mandelate salt is obtained.

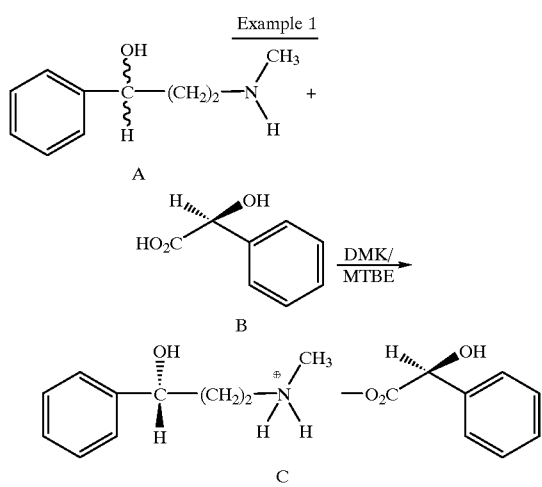

S-(+)-Mandelic acid B (10.37 g, 0.0682 mol) was added in one portion to a solution of PMAP A (25.0 g, 0.152 mol) in 200 mL dimethylketone (DMK) and 200 mL of MTBE. The solution was heated to 50° C., and the solution was seeded with authentic N-methyl-3 R-hydroxy-3-phenylpropylamine S-(+)-mandelate salt C . The mixture was stirred for 1 hour and then was cooled over one hour to room temperature where it was stirred for 16 hours. The mixture was filtered and crystals obtained were washed with 75 mL 1.5:1 MTBE:acetone. 13.5 grams of C were recovered for a calculated yield of 28% based on PMAP. The enantiomeric excess was 93.%.

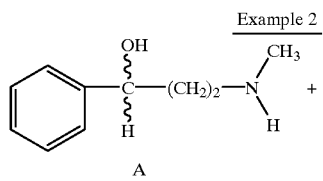

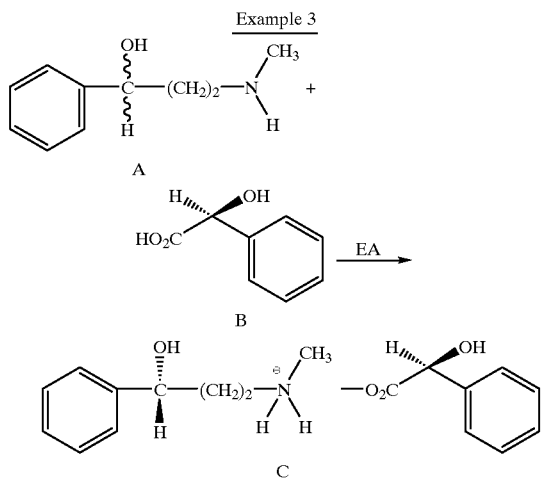

PMAP A (400.0 g, 2.42 mol) was placed in a flask containing 6.5 L of ethyl acetate (EA). A solution of (+)-mandelic acid B (165.7 g, 1.09 mol) in 1.5 L ethyl acetate was added to the PMAP solution over 10–15 minutes. After addition, the reaction mixture was heated to 50° C. at which point all the solids had dissolved. The solution was slowly cooled to 39–40° C. and seeded with authentic C . The reaction was cooled to ambient temperature and the crystals were collected by filtration. The crystals were washed with 4.0 L of ethyl acetate and dried in a vacuum oven at 35–40° C. A total of 226.4 g (29.5% yield) of C were obtained. The enantiomeric excess was determined on a derivative to be 94.0 %. Recrystallization of C .

C (226.4 g) was placed in a flask with acetone (2.9 L) and MTBE (0.90 L) and the mixture was heated to 50° C. The reaction was seeded with authentic C and the mixture was cooled to room temperature. The crystals were collected by filtration, washed with 0.905 L of 1:1 acetone/MTBE and dried in a vacuum oven at 35–40° C. A total of 186.5 g of N-methyl-3 R-hydroxy-3-phenylpropylamine S-(+)-mandelate salt (C) were collected. The enantiomeric excess was determined on to be 99.9%.

MS: 166 (M+1)

$^1$H NMR (CDCl$_3$): δ 7.45–7.15 (m, 10 H), 4.88 (s, 1 H), 4.67 (dd, 1 H), 2.85–2.60 (m, 2 H), 2.20 (s, 3 H), 1.92·1.75 (m, 2 H). EA: Calcd. for C$_{18}$H$_{23}$NO$_4$: Theory: C, 68.12; H, 7.30; N, 4.41. Found: C, 68.31; H, 7.14; N, 4.62.

EXAMPLE 4

N-methyl-3 R-hydroxy-3-phenylpropylamine S-(+)-mandelate salt (C) (275.0 g, 0.87 mol) was dissolved in 1.925 L MTBE and 0.55 L water and the pH was adjusted to 12.7 through the addition of 50% aqueous NaOH (46.1 ml). The resulting biphasic mixture was stirred for 5 minutes, and the layers were separated. The aqueous layer was back extracted with 1.1 L MTBE. The combined MTBE layers were washed with 0.55 L saturated aqueous NaCl, dried over Na$_2$SO$_4$, filtered and concentrated in vacuo to provide 133.7 g of N-methyl-3 R-hydroxy-3-phenylpropylamine D.

Step B:

A 1 L jacketed flask was charged with NaH (60 % oil dispersion, 31.7 g, 0.792 mol), potassium benzoate (13.0 g, 0.0809 mol ), and DMSO (133.6 mL). To this vessel was added a solution N-methyl-3 R-hydroxy-3-phenylpropylamine (133.6 g, 0.809 mol) in 133.6 mL DMSO over 45 minutes followed by a 66.8 mL DMSO rinse. The resulting mixture stirred for 10 minutes. To this vessel was added 2-fluorothioanisole (126.5 g, 0.890 mol) followed by an additional rinse with 66.8 mL of DMSO. The reaction mixture was heated to 65° C. and stirred for 18.8 hours. The reaction was then cooled to room temperature and added to a quench solution consisting of 0.9 L of H$_2$O and 0.7 L ethyl acetate followed by an additional rinse with 0.23 L H$_2$O and 0.18 L ethyl acetate. The layers were separated and the aqueous layer was extracted with 0.38 L ethyl acetate. The combined ethyl acetate layers were washed with 0.67 L each of H$_2$O and saturated aqueous NaCl. The ethyl acetate layer was dried over Na$_2$SO$_4$ and filtered. The Na$_2$SO$_4$ was washed with 0.13 L ethyl acetate. The filtrate was cooled to approximately 0° C. and HCl (g) (29.52 g) was added. The thick slurry thus formed was stirred an additional 30 minutes and the crystals were collected by filtration, washed with 0.27 L of cold ethyl acetate, and placed in a vacuum oven at 35–40° C. G (233.1 g) was recrystallized from EtOH (0.700 L) which provided 188.3 g of N-methyl3 R-(2-methylthiophenoxy)-3-phenylpropylamine hydrochloride in 99.6% ee.

$^1$H NMR (CDCl$_3$): δ 9.64 (br s, 2 H), 7.40–7.20 (m, 5 H), 7.15–7.05 (m, 1 H), 6.95–6.82 (m, 2 H), 6.65–6.55 (m, 1 H), 5.45 (dd, 1 H), 3.32–3.18 (m, 2 H), 2.66 (t, 3 H), 2.56–2.42 (m, 5 H). Calcd. for C$_{17}$H$_{22}$ClNOS:

Theory: C 63.04; H. 6.85; N. 4.33;

Found: C 63.34; H. 6.62; N. 4.47.

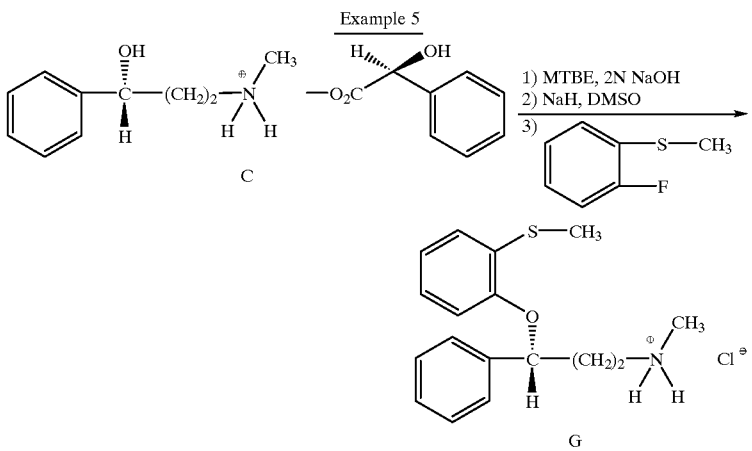

Example 5

N-methyl-3 R-hydroxy-3-phenylpropylamine S-(+)-mandelate salt (C) (9.16 grams, 28.81 mmol) was slurried in a mixture of MTBE (70 mL) and deionized H$_2$O (20 mL). 2 N NaOH (15 mL) was added to convert the salt to the free base. Upon addition of the NaOH, the phases separated. The aqueous layer was extracted with MTBE (20 mL, approx 2 vol.). The organic layers were combined and dried over Na$_2$SO$_4$, then the layers were filtered and concentrated in vacuo. The concentrated oil was dissolved in DMSO (3.75 mL).

60% Sodium hydride (0.691 g, 28.81 mmol) was added to DMSO (4.75 mL) at room temperature of about 25° C. The DMSO/concentrated oil mixture from the previous paragraph was added dropwise (internal temperature rose to 38° C.) over five minutes. The flask containing the DMSO/concentrated oil mixture was rinsed twice (each rinse was 1 mL of DMSO). This rinse DMSO was added to the sodium hydride/DMSO mixture. The solution was heated to 40° C. for 20 minutes. 2-fluoro-methylthiobenzene E (4.09 g, 28.81 mmol) in DMSO (2 mL) was added dropwise. The flask containing the DMSO/E mixture was rinsed twice (each rinse was 1 mL of DMSO). This rinse DMSO was added to the sodium hydride/DMSO mixture. The solution was heated to 53° C. and stirred for 49 hours.

An $^1$H-NMR spectrum of an aliquot (taken after ethyl acetate/water quench) showed approximately 10% N-methyl-3 R-hydroxy-3-phenylpropylamine D, and some 2-fluorothioanisole and some product. Another 0.05 equivalents (58 mg) of NaH were added and the reaction proceeded for an addition 21 hours at 53° C. $^1$H-NMR analysis of an aliquot (taken after ethyl acetate/water quench) showed the reaction was complete. The solution was diluted with 45 mL (approximately 9 volumes) of H$_2$O and 35 mL (approximately 7 volumes) ethyl acetate. The phases did separate with an emulsion layer. The layers were separated (the emulsion layer was kept with the organic layer). The aqueous layer was extracted with 3 volumes of ethyl acetate and this ethyl acetate extraction was added to the organic layer/emulsion mixture. The now combined organic layers were then washed twice with 5 volumes of dilute aqueous NaCl. To the organic layers was now added 28.81 mL 1 M HCl in diethyl ether. Crystals formed almost immediately. The liquid was cooled to 0° C. and stirred 15 minutes. The crystals were filtered off and washed with 25 mL of ethyl acetate. The crystals were placed in a vacuum oven at 45° C. for 24 hours. The yield was 8.1 grams (87%) of N-methyl-3 R-(2-methylthiophenoxy)-3-phenylpropylamine hydrochloride salt. %ee=92.

The N-methyl-3 R-(2-methylthiophenoxy)-3-phenylpropylamine hydrochloride salt crystals formed above (8.0 g) were placed in ethanol (24 mL). The ethanol was heated to approximately 75° C. and stirred for 30 minutes to dissolve the crystals. The ethanol was cooled to 65° C. and seeded with authentic N-methyl-3 R-(2-methylthiophenoxy)-3-phenylpropylamine hydrochloride salt. After seeding crystals formed rather rapidly. The ethanol was stirred at 65° C. for twenty minutes and then cooled over 1 hour to room temperature and then to 0° C. for one hour. The ethanol was filtered, crystals collected and then washed with 20 mL ethanol. The yield of N-methyl-3 R-(2-methylthiophenoxy)-3-phenylpropylamine hydrochloride salt was 6.25 grams (78%). %ee=99.3.

EXAMPLE 6

Using either of the methods described in Examples 4 or 5 above (see also Koenig, et al., *Tetrahedron Letters*, 35(9), 1339 (1994); Chenevert, et al., *Chemistry Letters*, 1603 (1991); Kumar, et al., *Tetrahedron Letters*, 32(16), 1901 (1991); Gao and Sharpless, *J. Org. Chem.*, 53, 4081 (1988)) and employing the appropriate N-methyl-3 R(or 3 S)-hydroxy-3-phenylpropylamine S-(+)- (or R-(-))-mandelate salt and either 4-chloro-trifluoromethylbenzene or 2-fluorotoluene can be prepared (R)-fluoxetine, (S)-fluoxetine or tomoxetine or their pharmaceutically acceptable salts.

Determination of Enantiomeric Excess for Examples 1–6

20 mg of the subject salt is combined with 5 mL Adichloromethane and 5 mL saturated aqueous sodium bicarbonate. After shaking well for 2 minutes, 20 μL of acetyl chloride are added and the resulting mixture shaken well for an additional 2 minutes. The organic phase is separated, dried over sodium sulfate, and concentrated under reduced pressure. The residual oil is dissolved in 6–10 mL of 95:3:2 UV grade hexane:n-propanol:UV grade methanol. This solution is analyzed on a Chiral pak AS 4.6 mm×25 cm column, eluting with of 95:3:2 UV grade hexane:n-propanol:UV grade methanol at a rate of 1 mL/min in a 40oC column. The eluant was analyzed at 210 nm. The N-acetylated (R)-enantiomer is the faster eluting enantiomer under these conditions.

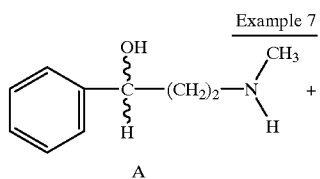

Example 7

A

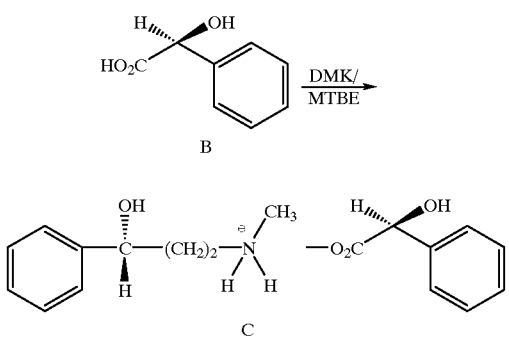

B

C (R,S)-N-Methyl-3-hydroxy-3-phenylpropylamine A (PMAP) (150.0 g, 837.5 mmol), acetone (1125 mL), and methyl t-butyl ether (1125 mL) were combined. S-(+)-Mandelic acid B (57.34 g, 376.9 mmol) was added and the mixture heated to reflux. After 2.5 hours, the mixture was slowly cool to ambient temperature over about 2 hours to give a solid. The solid was collected by filtration, rinsed with acetone/methyl t-butyl ether (1/1, 600 mL), and dried to give the compound C (100.5 g): HPLC, Chiralcel OD-H column (150 mm×4.6 mm) at 35° C., detection at 258 nm, eluting with hexane-isopropanol-diethyl amine 96.8:3:0.2 at 1 mL/min, tR=9.0 min (R) enantiomer; tR (S) enantiomer=15 min, 93%ee.

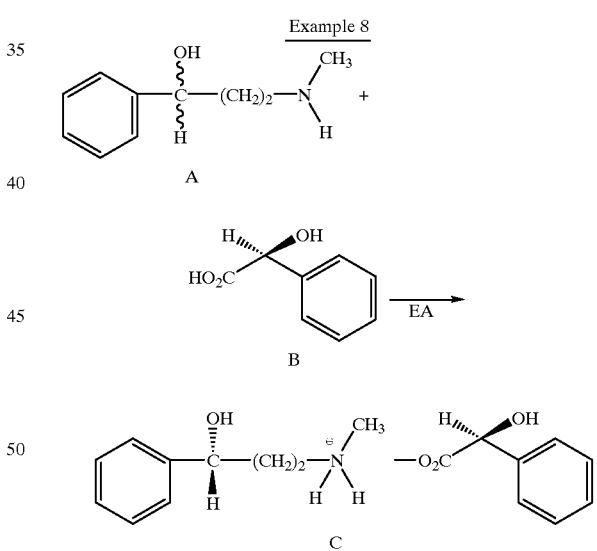

Example 8

A

B

C (R,S)-N-Methyl-3-hydroxy-3-phenylpropylamine A (PMAP) (800 g, 4.8 mol) was stirred with ethyl acetate (11.2 L) to form a solution. An ethyl acetate (4.8 L) solution of (S)-(+)-mandelic acid B (331 g, 2.16 mol) was added to the solution at ambient temperature and the resulting reaction mixture heated to about 50° to 55° C. for 1 hour. The solution was then cooled, seeded and stirred for 2 hour at about 44° to 48° C. and slowly to ambient temperature with stirred for 2 to 20 h at that temperature. After stirring, the slurry was filtered, then dried at 50° C. to afford the compound C 471 g (30.7% yield, 95% ee).

Example 9

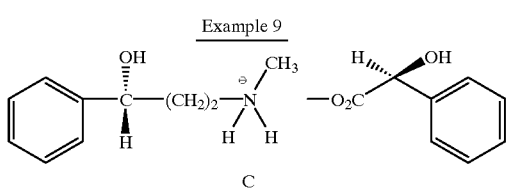

C (R)-N-Methyl-3-hydroxy-3-phenylpropylamine mandelate C (940 g. 2.96 mol) was heated to about 50° to 55° C with t-butyl methyl ether (3.8 L) and acetone (12.3 L) to form a solution. The solution was cooled and seeded to give a slurry and the resulting slurry filtered to provide a solid after drying at 50° C. to yield the title compound 795 g (85* yield, 100% ee).

Example 10

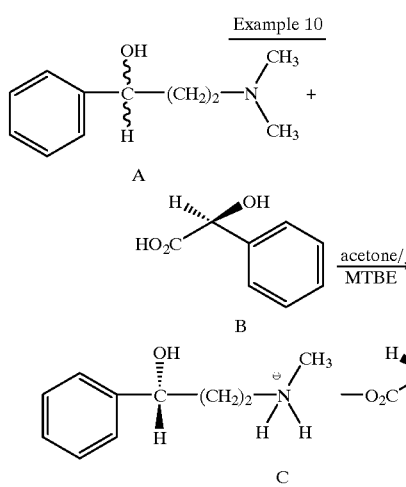

N,N-Dimethyl-3 R,S-hydroxy-3-phenylpropylamine A (150.0 g, 837.5 mmol), acetone (1125 mL), and methyl t-butyl ether (1125 mL) were combined. R-(−)-Mandelic acid (57.34 g, 376.9 mmol) was added in one portion. The solution was heated to reflux. After 2.5 hours, the reaction mixture was slowly cooled to ambient temperature over about 2 hours to give a solid. The solid was collected by filtration and rinse with acetone/methyl t-butyl ether (1/1, 600 mL) to give, after drying, compound C (100.5 g): HPLC, Chiralcel OD-H column (150 mm×4.6 mm) at 35° C., detection at 258 nm, eluting with hexane-isopropanol-diethyl amine 96.8:3:0.2 at 1 mL/min, tR=9.0 min (R) enantiomer; tR (S) enantiomer=15 min, 93%ee.

Example 11

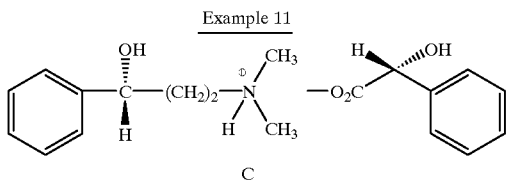

C (R)-N,N-Dimethyl-3-hydroxy-3-phenylpropylamine-(+)-mandelic acid salt (97.5 g) and ethanol (1.0 L) were combined and heated to about 55° C. Methyl t-butyl ether (400 mL) was added. The reaction mixture was cooled in an ice-bath with stirring to give a solid. The solid was collected by filtration to give, after drying, compound C. HPLC; Chiralcel OD-H column (150 mm×4.6 mm) at 35° C., detection at 258 nm, eluting with hexane-isopropanol-diethyl amine 96.8:3:0.2 at 1 mL/min, tR (R) enantiomer=9.0 min, tR (S) enantiomer=15 min, 99%ee.

Example 12

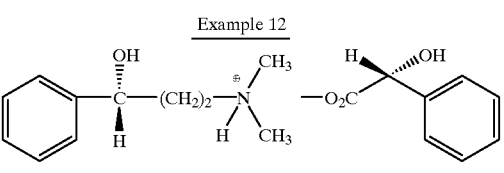

C

N,N-dimethyl-R3-hydroxy-3-phenylpropylamine mandelic acid salt (39.0 g) and dichloromethane (390 mL), and an aqueous 0.3 M sodium hydroxide solution (500 mL) were combined with stirring. After 10 minutes, the layers were separated, the organic layer was combined with an aqueous 0.05 M sodium hydroxide solution (500 mL) and stirred. Then the layers were separated, the organic layer was dried over 4Å molecular sieves, filtered, and evaporated to give the compound C (19.83 g): HPLC, Zorbax $C_{18}$, detection at 220 nm, eluting with acetonitrile-water 2:1 containing 0.1% TFA at 2 mL/min, tR=1.2 min (R)-enantiomer 99.9%ee. $^1$H NMR (CDCl$_3$) characteristic resonances at δ 4.83 (dd, 1 H), 2.27 (s, 6 H).

EXAMPLE 13

Using either of the methods described in Examples 4 or 5 above (see also Koenig, et al., *Tetrahedron Letters*, 35(9), 1339 (1994); Chenevert, et al., *Chemistry Letters*, 1603 (1991); Kumar, et al., *Tetrahedron Letters*, 32(16), 1901 (1991); Gao and Sharpless, *J. Orq. Chem.*, 53, 4081 (1988)) and employing the appropriate N,N-dimethyl-3 R(or 3 S)-hydroxy-3-phenylpropylamine R-(−)- (or S-(+))-mandelate salt and either 4-chloro-trifluoromethylbenzene, followed by N-demethylation as is well known and appreciated in the art and which includes demethylations which proceed through a N-cyano and carbamate intermediates followed by hydrolysis (see for example, U.S. Pat. Nos. 4,956,388; 4,314,081; and 5,362,886) one can be prepared R-fluoxetine or S-fluoxetine and their pharmaceutically acceptable salts.

The present invention has been described in detail, including the preferred embodiments thereof. However, it will be appreciated that those skilled in the art, upon consideration of the present disclosure, may rake modifications and/or improvements that fall within the scope and spirit of the invention as set forth in the following claims.

What is claimed is:

1. A process to make the S-(+)-mandelic acid salt of N-methyl-3 R-hydroxy-3-phenylpropylamine comprising reacting N-methyl-3(R,S)-hydroxy-3-phenyipropylamine with S-(+)-mandelic acid.

2. A process to make the R-(−)-mandelic acid salt of N-methyl-3 S-hydroxy-3-phenylpropylamine comprising reacting N-methyl-3(R,S)-hydroxy-3-phenylpropylamine with R-(−)-mandelic acid.

3. A compound of the formula:

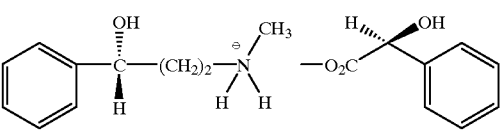

which is named N-methyl-3 R-hydroxy-3-phenylpropylamine S-(+)-mandelate salt.

4. A compound of the formula:

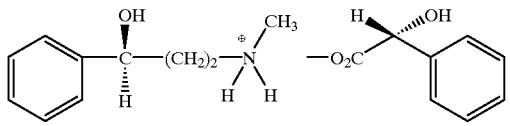

which is named N-methyl-3 S-hydroxy-3-phenylpropylamine R-(−)-mandelate salt.

5. A process to make the R-(−)-mandelic acid salt of N,N-dimethyl-3 R-hydroxy-3-phenylpropylamine comprising reacting N,N-dimethyl-3(R,S)-hydroxy-3-phenylpropylamine with R-(−)-mandelic acid.

6. A process to make the S-(+)-mandelic acid salt of N,N-dimethyl-3 S-hydroxy-3-phenylpropylamine comprising reacting N,N-dimethyl-3(R,S)-hydroxy-3-phenylpropylamine with S-(+)-mandelic acid.

7. A compound of the formula:

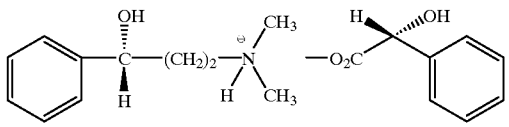

which is named N,N-dimethyl-3 R-hydroxy-3-phenylpropylamine R-(−)-mandelate salt.

8. A compound of the formula:

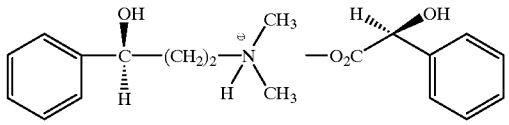

which is named N,N-dimethyl-3 S-hydroxy-3-phenylpropylamine S-(+)-mandelate salt.

* * * * *